(12) United States Patent
Knapp

(10) Patent No.: US 8,486,293 B2
(45) Date of Patent: Jul. 16, 2013

(54) HYDROGEN FLUORIDE-HFC-254EB AZEOTROPE AND ITS USES

(75) Inventor: Jeffrey P. Knapp, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 408 days.

(21) Appl. No.: 12/898,983

(22) Filed: Oct. 6, 2010

(65) Prior Publication Data

US 2011/0101264 A1 May 5, 2011

Related U.S. Application Data

(60) Provisional application No. 61/256,340, filed on Oct. 30, 2009.

(51) Int. Cl.
*C09K 5/04* (2006.01)

(52) U.S. Cl.
USPC .............................. 252/67; 510/408

(58) Field of Classification Search
USPC ............................ 252/67; 510/408
See application file for complete search history.

(56) References Cited

U.S. PATENT DOCUMENTS

2006/0106263 A1* 5/2006 Miller et al. .................. 570/155

FOREIGN PATENT DOCUMENTS

| WO | WO2009093047 A2 | 7/2009 |
| WO | WO2009105517 A2 | 8/2009 |

OTHER PUBLICATIONS

William Schotte, Ind. Chem. Process Des. Dev. (1980) 19, pp. 432-439, "Collection of Phase Equilibrium Data for Separation Technology".
Internation Search Report for PCT/US2010/052237, Feb. 3, 2011.

* cited by examiner

*Primary Examiner* — Douglas McGinty

(57) ABSTRACT

Described is a process for separating 1,1,1,2-tetrafluoropropane and hydrogen fluoride from a mixture comprising 1,1,1,2-tetrafluoropropane, 1,1,1,2,3-pentafluoropropane and hydrogen fluoride comprising: subjecting said 1,1,1,2-tetrafluoropropane, 1,1,1,2,3-pentafluoropropane and hydrogen fluoride mixture to a distillation step, forming a column distillate composition comprising an azeotropic or near-azeotropic composition of said 1,1,1,2-tetrafluoropropane and hydrogen fluoride, and a bottoms composition of 1,1,1,2,3-pentafluoropropane. The column distillate may optionally be made essentially free of 1,1,1,2,3-pentafluoropropane and the column bottoms composition may optionally be made essentially free of HF. Also described is a process for separating 1,1,1,2-tetrafluoropropane and hydrogen fluoride from a mixture of 1,1,1,2-tetrafluoropropane and hydrogen fluoride. Also described are azeotropic and azeotrope-like compositions comprising 1,1,1,2-tetrafluoropropane and hydrogen fluoride.

8 Claims, 2 Drawing Sheets

HYDROGEN FLUORIDE-HFC-254EB AZEOTROPE AND ITS USES

BACKGROUND INFORMATION

1. Field of the Disclosure

This disclosure relates in general to methods of synthesis of hydrofluoroolefins.

2. Description of the Related Art

The refrigeration industry has been working for the past few decades to find replacement refrigerants for the ozone depleting chlorofluorocarbons (CFCs) and hydrochlorofluorocarbons (HCFCs) being phased out as a result of the Montreal Protocol. The solution for most refrigerant producers has been the commercialization of hydrofluorocarbon (HFC) refrigerants. The new HFC refrigerants, HFC-134a being the most widely used at this time, have zero ozone depletion potentials and thus are not affected by the current regulatory phase-out as a result of the Montreal Protocol.

In addition to ozone depleting concerns, global warming is another environmental concern. In the not too distant future, hydrofluorocarbons with high calculated global warming potential will be phased out. As well. Thus, there is a need for heat transfer compositions that meet both low ozone depletion and low global warming potentials. Certain hydrofluoroolefins meet both goals. Thus there is a need for manufacturing processes that provide halogenated hydrocarbons and fluoroolefins that contain no chlorine and also have a lower global warming potential.

SUMMARY

The present invention describes azeotrope and azeotrope-like compositions of 1,1,1,2-tetrafluoropropane and hydrogen fluoride. Described herein are processes for separating 1,1,1,2-tetrafluoropropane from a mixture comprising 1,1,1,2-tetrafluoropropane, 1,1,1,2,3-pentafluoropropane and hydrogen fluoride comprising subjecting said 1,1,1,2-tetrafluoropropane, 1,1,1,2,3-pentafluoropropane and hydrogen fluoride mixture to a distillation step, forming a column distillate composition comprising an azeotropic or near-azeotropic composition of said 1,1,1,2-tetrafluoropropane and hydrogen fluoride, and a bottoms composition of 1,1,1,2,3-pentafluoropropane essentially free of hydrogen fluoride.

Also described herein are processes for the separation of 1,1,1,2-tetrafluoropropane from a mixture comprising an azeotropic or near-azeotropic composition of 1,1,1,2-tetrafluoropropane and hydrogen fluoride, said process comprising subjecting said mixture to a first distillation step in which a composition enriched in either (i) hydrogen fluoride or (ii) 1,1,1,2-tetrafluoropropane is removed as a first distillate composition with a first bottoms composition being enriched in the other of said components (i) or (ii); and subjecting said first distillate composition to a second distillation step conducted at a different pressure than the first distillation step in which the component enriched as a first bottoms composition in the first distillation is removed in a second distillate with a second bottoms composition enriched in the same component which was enriched in the first distillate composition.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1:
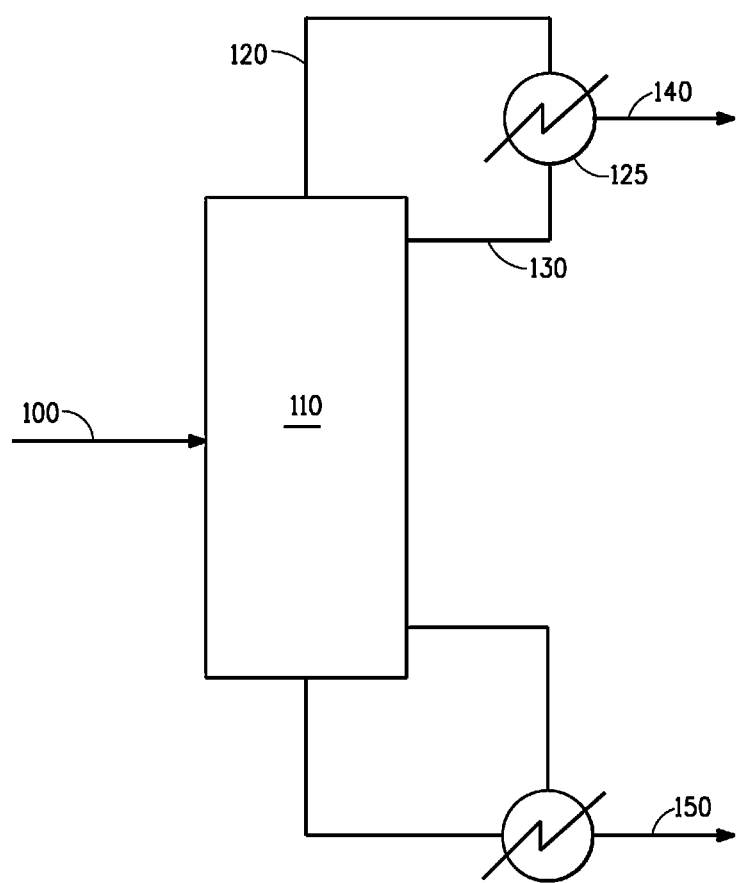
FIG. 1 includes an illustration of a distillation process for the separation of 1,1,1,2-tetrafluoropropane and hydrogen fluoride from 1,1,1,2,3-pentafluoropropane, 1,1,1,2,3-pentafluoro-2-chloropropane and other compounds.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Described herein are azeotropic and azeotrope-like compositions of 1,1,1,2-tetrafluoropropane and hydrogen fluoride. Described herein are processes for separating 1,1,1,2-tetrafluoropropane from a mixture comprising 1,1,1,2-tetrafluoropropane, 1,1,1,2,3-pentafluoropropane and hydrogen fluoride comprising subjecting said 1,1,1,2-tetrafluoropropane, 1,1,1,2,3-pentafluoropropane and hydrogen fluoride mixture to a distillation step, forming a column distillate composition comprising an azeotropic or near-azeotropic composition of said 1,1,1,2-tetrafluoropropane and hydrogen fluoride, and a bottoms composition of 1,1,1,2,3-pentafluoropropane, essentially free of hydrogen fluoride.

Also described herein are processes for the separation of 1,1,1,2-tetrafluoropropane from a mixture comprising an azeotropic or near-azeotropic composition of 1,1,1,2-tetrafluoropropane and hydrogen fluoride, said process comprising subjecting said mixture to a first distillation step in which a composition enriched in either (i) hydrogen fluoride or (ii) 1,1,1,2-tetrafluoropropane is removed as a first distillate composition with a first bottoms composition being enriched in the other of said components (i) or (ii); and subjecting said first distillate composition to a second distillation step conducted at a different pressure than the first distillation step in which the component enriched as a first bottoms composition in the first distillation is removed in a second distillate with a second bottoms composition enriched in the same component which was enriched in the first distillate composition. In some embodiments, the composition to be separated contains additional 1,1,1,2-tetrafluoropropane, or hydrogen fluoride, beyond the amount necessary to from the azeotropic or azeotrope-like composition.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms.

As used herein, an azeotropic composition is a constant boiling liquid admixture of two or more substances wherein the admixture distills without substantial composition change and behaves as a constant boiling composition. Constant boiling compositions, which are characterized as azeotropic, exhibit either a maximum or a minimum boiling point, as compared with that of the non-azeotropic mixtures of the same substances. Azeotropic compositions as used herein include homogeneous azeotropes which are liquid admixtures of two or more substances that behave as a single substance, in that the vapor, produced by partial evaporation or distillation of the liquid, has the same composition as the liquid. Azeotropic compositions as used herein also include heterogeneous azeotropes where the liquid phase splits into two or more liquid phases. In these embodiments, at the azeotropic point, the vapor phase is in equilibrium with two liquid phases and all three phases have different compositions. If the two equilibrium liquid phases of a heterogeneous azeotrope are combined and the composition of the overall liquid phase calculated, this would be identical to the composition of the vapor phase.

For the purpose of this discussion, near-azeotropic composition means a composition that behaves like an azeotrope (i.e., has constant boiling characteristics or a tendency not to fractionate upon boiling or evaporation). Thus, the composition of the vapor formed during boiling or evaporation is the same as or substantially the same as the original liquid composition. Hence, during boiling or evaporation, the liquid composition, if it changes at all, changes only to a minimal or negligible extent. This is to be contrasted with non-azeotropic compositions in which during boiling or evaporation, the liquid composition changes to a substantial degree.

Near-azeotropic compositions exhibit dew point pressure and bubble point pressure with virtually no pressure differential. That is to say that the difference in the dew point pressure and bubble point pressure at a given temperature will be a small value. It may be stated that compositions with a difference in dew point pressure and bubble point pressure of less than or equal to 3 percent (based upon the bubble point pressure) may be considered to be a near-azeotropic.

It is also recognized that both the boiling point and the weight percentages of each component of the azeotropic or near-azeotropic liquid composition may change when the azeotropic or near-azeotropic liquid composition is subjected to boiling at different pressures. Thus, an azeotropic or a near-azeotropic composition may be defined in terms of the unique relationship that exists among the components or in terms of the compositional ranges of the components or in terms of exact weight percentages of each component of the composition characterized by a fixed boiling point at a specified pressure. It is also recognized in the art that various azeotropic compositions (including their boiling points at particular pressures) may be calculated (see, e.g., W. Schotte Ind. Eng. Chem. Process Des. Dev. (1980) 19, 432-439). Experimental identification of azeotropic compositions involving the same components may be used to confirm the accuracy of such calculations and/or to modify the calculations at the same or other temperatures and pressures.

In one embodiment, the process is one to manufacture 1,1,1,2,3-pentafluoropropane, an intermediate useful in the manufacture of 2,3,3,3-tetrafluoro-1-propene, and in particular remove impurities of 1,1,1,2-tetrafluoropropane. In another embodiment, the process is one to remove hydrogen fluoride from mixtures comprising 1,1,1,2-tetrafluoropropane, 1,1,1,2,3-pentafluoropropane and hydrogen fluoride. In some embodiments, 1,1,1,2-tetrafluoropropane is produced as a by-product in the hydrogenation of 1,1,1,2,3-pentafluoro-2,3,3-trichloropropane to produce 1,1,1,2,3-pentafluoropropane.

In one embodiment, 1,1,1,2,3-pentafluoropropane is prepared by hydrogenation of 1,1,1,2,3-pentafluoro-2-propene. In another embodiment, 1,1,1,2,3-pentafluoropropene is prepared by hydrogenation of 1,1,1,2,3-pentafluoro-2,3,3-trichloropropane (CFC-215bb). In some embodiments, hydrogen fluoride is produced as a by-product via the unintended dehydrofluorination of 1,1,1,2,3-pentafluoropropane over a hydrogenation catalyst, to produce 1,1,1,2-tetrafluoropropene and hydrogen fluoride. Under the hydrogenation conditions, 1,1,1,2-tetrafluoropropene is hydrogenated to 1,1,1,2-tetrafluoropropane. In some embodiments, hydrogen fluoride is produced as a by-product via the over hydrogenation of 1,1,1,2,3-pentafluoropropane which produces 1,1,1,2-tetrafluoropropane.

In one embodiment, for the preparation of 1,1,1,2,3-pentafluoropropane, and the isolation of 1,1,1,2,3-pentafluoropropane the 1,1,1,2-tetrafluoropropane forms an azeotrope with HF. Hydrogen fluoride and 1,1,1,2,3-pentafluoropropane also are known to form an azeotrope, which may make difficult their separation by distillation.

In one embodiment, provided is a composition, which comprises 1,1,1,2-tetrafluoropropane and an effective amount of hydrogen fluoride (HF) to form an azeotropic composition. By effective amount is meant an amount, which, when combined with 1,1,1,2-tetrafluoropropane, results in the formation of an azeotropic or near-azeotropic mixture.

In consideration of the treatment of the effluent from a reactor and isolation of the products, in one embodiment, the reactor effluent comprises 1,1,1,2-tetrafluoropropane, 1,1,1,2,3-pentafluoropropane and hydrogen fluoride. One embodiment of a distillation process to separate such a mixture is illustrated in FIG. 1. In one embodiment, stream 100 is a representative composition leaving the hydrogenation reactor where 1225ye is converted to 245eb at high conversion (so that there is essentially no unreacted 1225ye remaining). Partially cooled & condensed stream 100 is fed to the middle of distillation column 110, which contains 40 theoretical stages and operates with a top pressure of 80 psig (94.7 psia). In column 110, the HF/254eb azeotrope is used to remove HF from the 245eb-rich feed mixture with very little loss of 245eb. The vapors 120 leaving the top of column 110 are partially condensed in condenser 125 with the resulting condensate 130 returned to the top of 110 as reflux. The noncondensed portion of 120 leaving 125 are removed as distillate 140. Distillate 140 contains essentially all of the HF and 254eb present in feed 100, but only a very small fraction of the 245eb in 100. The operating mass ratio of 130 to 100 is approximately 2.5:1. Essentially all of the 245eb in 100 is removed from the bottom of 110 as the bottoms product via stream 150. Stream 150 is essentially free of both HF and 254eb, demonstrating that the HF/254eb azeotrope has successfully removed HF from the azeotrope formed by HF and 245eb.

In one embodiment, depending on the degree of conversion of 1,1,1,2,3-pentafluoro-2,3,3-trichloropropane to 1,1,1,2,3-pentafluoropropane and dehydrofluoroination side reactions, or the degree of conversion of 1,1,1,2,3-pentafluoropropene to 1,1,1,2,3-pentafluoropropane, there may be enough hydrogen fluoride present so that all the 1,1,1,2-tetrafluoropropane in the overhead column distillate fraction is as it's azeotrope with hydrogen fluoride. In other embodiments where the conversion of 1,1,1,2,3-pentafluoro-2,3,3-trichloropropane is low, there may be 1,1,1,2-tetrafluoropropane present in the overhead distillate fraction in an amount greater than that found in the 1,1,1,2-tetrafluoropropane/hydrogen fluoride azeotrope. In one embodiment where the amount of hydrogen fluoride present in the reactor product stream is less than the amount to form an azeotrope with all of the 1,1,1,2-tetrafluoropropane, hydrogen fluoride can be added to the reactor effluent as it passes into the distillation column.

Compositions may be formed that comprise azeotropic combinations of hydrogen fluoride with 1,1,1,2-tetrafluoropropane. In one embodiment, these include compositions comprising from about 37.8 mole percent to about 59.3 mole percent HF and from about 40.7 mole percent to about 62.2 mole percent 1,1,1,2-tetrafluoropropane (which forms an azeotrope boiling at a temperature from between about −40° C. and about 100° C. and at a pressure from between about 2.6 psi and about 345 psia). The calculated normal boiling point of the azeotropic combination is −5.1° C. The normal boiling point of 1,1,1,2-tetrafluoropropane is ~0° C.

In another embodiment, compositions may be formed that consist essentially of azeotropic combinations of hydrogen fluoride with 1,1,1,2-tetrafluoropropane. These include compositions consisting essentially of from about 37.8 mole percent to about 59.3 mole percent HF and from about 40.7 mole percent to about 62.2 mole percent 1,1,1,2-tetrafluoropropane (which forms an azeotrope boiling at a temperature from between about −40° C. and about 100° C. and at a pressure from between about 2.6 psia and about 345 psia.

In yet another embodiment, near-azeotropic compositions containing HF and 1,1,1,2-tetrafluoropropane may also be formed. Such near-azeotropic compositions comprise about 35.2 mole percent to about 78.4 mole percent 1,1,1,2-tetrafluoropropane and about 21.6 mole percent to about 64.8 mole percent HF at temperatures ranging from about −40° C. to about 100° C. and at pressures from about 2.66 psia to about 345.2 psia.

In yet another embodiment, near-azeotropic compositions may be formed which consist essentially of from about 35.2 mole percent to about 78.4 mole percent 1,1,1,2-tetrafluoropropane and about 21.6 mole percent to about 64.8 mole percent HF at temperatures ranging from about −40° C. to about 100° C. and at pressures from about 2.66 psia to about 345.2 psia.

At atmospheric pressure, the boiling points of hydrofluoric acid and 1,1,1,2-tetrafluoropropane are about 19.5° C. and about ~0° C., respectively. At atmospheric pressure, the boiling point of the azeotrope of 1,1,1,2-tetrafluoropropane and hydrogen fluoride is about −5.1° C. One of ordinary skill in the art would readily recognize that azeotropic compositions and near azeotropic compositions are not readily separated into pure components by ordinary fractional distillation.

In one embodiment, the HF/1,1,1,2-tetrafluoropropane azeotropic and near-azeotropic compositions are useful in processes to produce 1,1,1,2,3-pentafluoropropane, and in processes to purify 1,1,1,2,3-pentafluoropropane. In fact, the HF/1,1,1,2-tetrafluoropropane azeotropic and near-azeotropic compositions may be useful in any process that creates a composition containing 1,1,1,2-tetrafluoropropane and HF.

In one embodiment, azeotropic distillation with 1,1,1,2-tetrafluoropropane may be carried out to separate hydrogen fluoride from 1,1,1,2,3-pentafluoropropane. 1,1,1,2,3-pentafluoropropane may be converted to HFC-1234yf by dehydrofluorination, as disclosed herein. A two-column pressure-swing distillation may then be carried out to separate the HF from the 1,1,1,2-tetrafluoropropane by-product. HF may also be removed from the halogenated hydrocarbon components of the product mixture using, for example, standard aqueous solution scrubbing techniques. However, the production of substantial amounts of scrubbing discharge can create aqueous waste disposal concerns. Thus, there remains a need for processes for recovering HF from such product mixtures.

While the initial mixture treated in accordance with the processes disclosed herein can be obtained from a variety of sources, including by adding 1,1,1,2-tetrafluoropropane to HF-containing compositions, in one embodiment, an advantageous use of the present processes resides in treating the effluent mixtures from the preparation of 1,1,1,2,3-pentafluoropropane.

In one embodiment, another aspect provides a process for the separation of hydrogen fluoride from 1,1,1,2,3-pentafluoropropane comprising: a) forming a mixture of 1,1,1,2-tetrafluoropropane, 1,1,1,2,3-pentafluoropropane, and hydrogen fluoride; and b) subjecting said mixture to a distillation step forming a column distillate composition comprising an azeotropic or near-azeotropic composition of HF and 1,1,1,2-tetrafluoropropane, as an overhead stream, 120. In one embodiment, a bottoms stream, 150, from such a distillation comprises 1,1,1,2,3-pentafluoropropane essentially free of hydrogen fluoride. In another embodiment, a bottoms stream from such a distillation comprises 1,1,1,2,3-pentafluoropropane and 1,1,1,2-tetrafluoropropane. One embodiment of such a distillation setup is illustrated in FIG. 1.

In one embodiment, by "essentially free of hydrogen fluoride" is meant that the composition contains less than about 100 ppm (mole basis). In another embodiment, by "essentially free of hydrogen fluoride" is meant that the composition contains less than about 10 ppm. In yet another embodiment, by "essentially free of hydrogen fluoride" is meant that the composition contains less than about 1 ppm, of hydrogen fluoride.

This azeotropic distillation takes advantage of the low boiling azeotropic composition formed by 1,1,1,2-tetrafluoropropane and HF. The azeotropic composition boils at a temperature lower than the boiling point of either pure component and lower than the boiling point of the 1,1,1,2,3-pentafluoropropane/HF azeotrope.

As stated previously, the mixture of 1,1,1,2-tetrafluoropropane, 1,1,1,2,3-pentafluoropropane and HF may be formed by any practical means. In one embodiment, the present process is particularly useful for the separation of 1,1,1,2-tetrafluoropropane from the reaction mixture produced by the reaction of 1,1,1,2,3-pentafluoro-2,3,3-trichloropropane with hydrogen in the presence of a catalyst. In another embodiment, the present process is useful for the separation of hydrogen fluoride from the reaction mixture produced by the reaction of 1,1,1,2,3-pentafluoropropene with hydrogen in the presence of a catalyst. The reaction mixture produced may then be treated by the instant process to remove hydrogen fluoride.

In one embodiment, operating the present azeotropic distillation involves providing an excess of 1,1,1,2-tetrafluoropropane to the distillation column. If the proper amount of 1,1,1,2-tetrafluoropropane is fed to the column, then all the HF may be taken overhead as an azeotropic composition containing 1,1,1,2-tetrafluoropropane and HF. Thus, the 1,1,1,2,3-pentafluoropropane removed from the column bottoms will be essentially free of HF.

In one embodiment, by "essentially free of HF" is meant that the composition contains less than about 100 ppm (mole basis). In another embodiment, by "essentially free of HF" is meant that the composition contains less than about 10 ppm. In yet another embodiment, by "essentially free of HF" is meant that the composition contains less than about 1 ppm, of HF.

In one embodiment, in the distillation step, the distillate exiting the distillation column overhead comprising HF and 1,1,1,2-tetrafluoropropane may be condensed using, for example, standard reflux condensers. At least a portion of this condensed stream may be returned to the top of the column as reflux. The ratio of the condensed material, which is returned to the top of the distillation column as reflux, to the material removed as distillate is commonly referred to as the reflux ratio. The specific conditions which may be used for practicing the distillation step depend upon a number of parameters, such as the diameter of the distillation column, feed points, and the number of separation stages in the column, among others. The operating pressure of the distillation column may range from about 10 psi pressure to about 200 psi (1380 kPa), normally about 20 psi to about 50 psi. In one embodiment, the distillation column is operated at a pressure of about 25 psi (172 kPa) with a bottoms temperature of about 44° C. and a top temperature of about 6° C. Normally, increasing the reflux ratio results in increased distillate stream purity, but generally the reflux ratio ranges between 1/1 to 200/1. The temperature of the condenser, which is located adjacent to the top of the column, is normally sufficient to substantially condense the distillate that is exiting from the top of the column, or is that temperature required to achieve the desired reflux ratio by partial condensation.

In one embodiment, the column distillate composition comprising an azeotropic or near-azeotropic composition of HF and 1,1,1,2-tetrafluoropropane, essentially free of 1,1,1, 2,3-pentafluoropropane, must be treated to remove the HF and provide pure 1,1,1,2-tetrafluoropropane as product. This may be accomplished, for example, by neutralization or by a second distillation process, as described herein.

Figure 2:
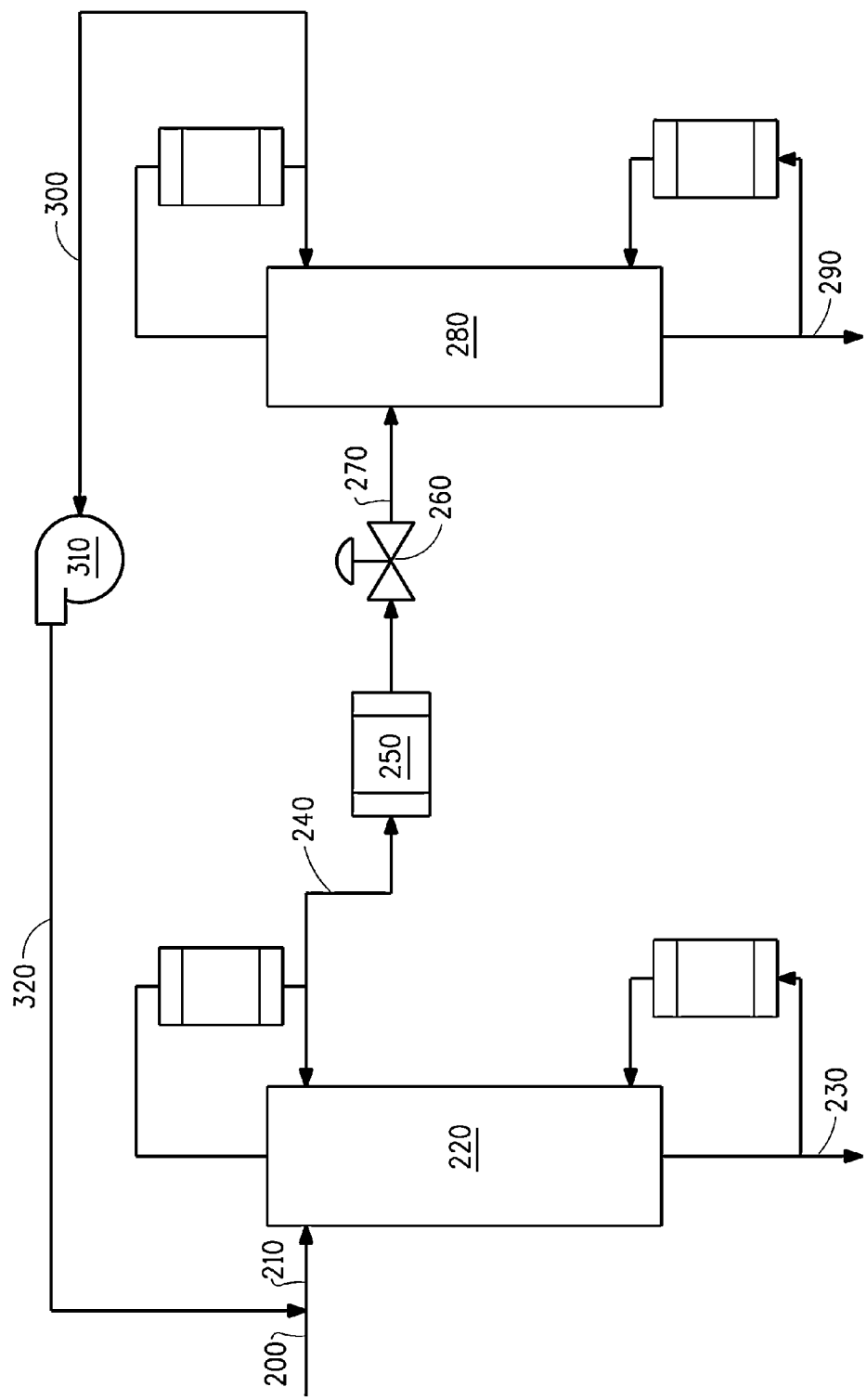
FIG. 2 includes an illustration for the separation of 1,1,1,2-tetrafluoropropane from the azeotrope of 1,1,1,2-tetrafluoropropane and hydrogen fluoride by pressure swing distillation.

In one embodiment, a further aspect provides a process for the separation of 1,1,1,2-tetrafluoropropane from a mixture comprising 1,1,1,2-tetrafluoropropane and HF, said process comprising: a) subjecting said mixture to a first distillation step in which a composition enriched in either (i) hydrogen fluoride or (ii) 1,1,1,2-tetrafluoropropane is removed as a first distillate composition with a first bottoms composition being enriched in the other of said components (i) or (ii); and b) subjecting said first distillate composition to a second distillation step conducted at a different pressure than the first distillation step in which the component enriched in the first bottoms composition in (a) is removed in a second distillate composition with a second bottoms composition enriched in the same component which was enriched in the first distillate composition. An embodiment of a pressure swing distillation process is illustrated in FIG. 2. The process as described above takes advantage of the change in azeotrope composition at different pressures to effect the separation of 1,1,1,2-tetrafluoropropane and HF. In one embodiment, the first distillation step is carried out at a higher pressure relative to the second distillation step. At higher pressures, the HF/1,1,1,2-tetrafluoropropane azeotrope contains more 1,1,1,2-tetrafluoropropane, or less HF. If the compositions of the feed to the first distillation step is HF-rich relative to the azeotropic composition at the higher pressure, then this high-pressure distillation step produces an excess of HF, which boiling at a higher temperature than the azeotrope will exit the column, 220, as the bottoms, 230, as essentially pure HF. The first column distillate, 240, whose composition approaches the azeotropic composition at the pressure of the first distillation step, is then fed to a second distillation step operating at lower pressure. At the lower pressure, the HF/1,1,1,2-tetrafluoropropane azeotrope shifts to lower concentrations of 1,1,1,2-tetrafluoropropane. Therefore, the feed to this second distillation step is rich in 1,1,1,2-tetrafluoropropane relative to the azeotrope at this lower pressure, so that the excess 1,1,1,2-tetrafluoropropane, having a boiling point higher than the azeotrope, exits the second distillation column as the bottoms composition, 290. The present process may be conducted in such as manner as to produce 1,1,1,2-tetrafluoropropane essentially free of HF. Additionally, the present process may be conducted in such a manner as to produce HF essentially free of 1,1,1,2-tetrafluoropropane.

In another embodiment, the first distillation step is carried out at a lower pressure relative to the second distillation step. At lower pressures, the HF/1,1,1,2-tetrafluoropropane azeotrope contains less 1,1,1,2-tetrafluoropropane. If the composition of the feed to the first distillation step is rich in 1,1,1, 2-tetrafluoropropane relative to the azeotropic composition at the pressure of the first distillation step, this low-pressure distillation step produces an excess of 1,1,1,2-tetrafluoropropane, which boiling at a higher temperature than the azeotrope will exit the column as the bottoms as essentially pure 1,1,1,2-tetrafluoropropane. The first column distillate, whose composition approaches the azeotropic composition at the first column's pressure, is then fed to a second distillation step operating at higher pressure. At the higher pressure, the HF/1, 1,1,2-tetrafluoropropane azeotrope shifts to higher concentrations of 1,1,1,2-tetrafluoropropane, or lower concentrations of HF. The feed to this second distillation step is now rich in HF relative to the azeotropic composition at the higher pressure so there is an excess of HF in the column. The excess HF, having a boiling point higher than the azeotrope, exits the second distillation column as the bottoms composition. The present process may be conducted in such as manner as to produce 1,1,1,2-tetrafluoropropane essentially free of HF. Additionally, the present process may be conducted in such a manner as to produce HF essentially free of 1,1,1,2-tetrafluoropropane.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, $81^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

EXAMPLES

The concepts described herein will be further described in the following examples, which do not limit the scope of the invention described in the claims.

Legend

1234yf is $CF_3CF=CH_2$
263fb is $CF_3CH_2CH_3$

235bb is $CF_3CFClCH_2F$
254eb is $CF_3CFHCH_3$
1225ye is E and Z forms of $CF_3CF=CHF$
1215yb is E and Z forms of $CF_3CF=CFCl$
1243zt is $CF_3CH=CH_2$
245eb is $CF_3CHFCH_2F$
226ea is $CF_3CHFCF_2Cl$
215bb is $CF_3CFClCFCl_2$ Example 1

Reaction of $H_2$ with CFC-215bb Over Palladium on Alumina Catalyst

A Hastelloy tube (0.625" OD×0.576 ID×10"L) was filled with 15 cc (9.7 g) of commercial 1% palladium on alumina spheres (4 mm). The packed portion of the reactor was heated by a 5.7"×1" ceramic band heater clamped to the outside of the reactor. A thermocouple, positioned between the reactor wall and the heater, measured the reactor temperature. The catalyst was activated by heating at 250° C. for 2 hours with 50 sccm ($8.33 \times 10^{-7}$ m$^3$/s) of nitrogen. The nitrogen was turned off and the catalyst was treated with 50 sccm ($8.33 \times 10^{-7}$ m$^3$/s) of hydrogen at 250° C. for two hours. The reactor was then cooled to the desired operating temperature under a flow of nitrogen. A flow of hydrogen and CFC-215bb was then started through the reactor after stopping the nitrogen flow. The hydrogen to CFC-215bb mole ratio was 2/1 and the contact time was 30 seconds. The products were analyzed by GC/MS and are reported in Table 1 as mole %. Minor amounts of other compounds, not listed in Table 1 were also present.

TABLE 1

| T° C. | 1234yf | Z-1225ye | E-1225ye | 245eb | 235bb | Z or E-1215yb | E or Z-1215yb | 254eb | 215bb |
|---|---|---|---|---|---|---|---|---|---|
| 175 | 7.0 | 25.6 | 24.1 | 8.9 | 7.4 | 5.2 | 3.8 | 14.1 | 1.0 |
| 250 | 4.3 | 33.4 | 14.7 | 1.4 | 2.0 | 16.7 | 8.7 | 6.4 | 0.4 |

Example 2

Reaction of $H_2$ with CFC-215bb Over Palladium on Carbon Catalyst

Example 1 was substantially repeated except that the catalyst was commercial 0.5% palladium on carbon (5.4 g, 15.0 ml) and only hydrogen and CFC-215bb were fed to the reactor. The hydrogen to CFC-215bb mole ratio was 2/1 and the contact time was 30 seconds. The GC/MS analytical results of the products, in area %, for various operating temperatures are summarized in Table 2. Minor amounts of other compounds, not listed in Table 2 were also present.

TABLE 2

| T° C. | 263fb | 254eb | 245eb | 235bb |
|---|---|---|---|---|
| 150 | 0.1 | 9.4 | 83.2 | 7.0 |
| 175 | 0.2 | 8.5 | 82.3 | 5.8 |
| 225 | 0.6 | 10.7 | 87.2 | 0.1 |

Example 3

Hydrogenation of 1,1,1,2,3-pentafluoropropene

An inconel tube (⅝ inch OD) was filled with 16 cc (14.45 gm) of 0.5% palladium on acid washed carbon (6×10 mesh). The catalyst was heated to 400° for 7 minutes under a nitrogen purge of 20 sccm ($3.33 \times 10^{-7}$ m$^3$/s) and then lowered to 100° for 13 minutes. The temperature was raised to 200° C. for 45 minutes under a nitrogen purge of 40 sccm ($6.67 \times 10^{-7}$ m$^3$/s). The flow of nitrogen was reduced to 20 sccm ($3.33 \times 10^{-7}$ m$^3$) and hydrogen introduced at 10 sccm ($1.67 \times 10^{-7}$ m$^3$/s) for 60 minutes. While maintaining the same nitrogen flow, hydrogen was increased to 20 sccm ($3.33 \times 10^{-7}$ m$^3$/s) for 30 minutes. While maintaining the flow of hydrogen, nitrogen was reduced to 10 sccm ($1.67 \times 10^{-7}$ m$^3$/s) for 60 minutes. The nitrogen was shut off and the hydrogen was increased to 40 sccm ($6.67 \times 10^{-7}$ m$^3$/s) for 130 minutes.

The temperature of the reactor was lowered to 85° C. and HFC-1225ye (1,2,3,3,3-pentafluoro-1-propene) was fed at 61 sccm ($1.02 \times 10^{-6}$ m$^3$/s) and hydrogen at 85 sccm ($1.42 \times 10^{-6}$ m$^3$/s). The effluent of the reactor was analyzed by GCMS to contain 92% HFC-245eb (1,1,1,2,3-pentafluoropropane and 8% HFC-254eb (1,1,1,2-tetrafluoropropane).

Referring to FIG. 1, stream 100 is a simplified "typical" composition leaving a hydrogenation reactor where 1225ye is converted to 245eb at high conversion (so that there is essentially no unreacted 1225ye remaining).

Partially cooled & condensed stream 100 is fed to distillation column 110, which contains 40 theoretical stages and operates with a top pressure of 80 psig (94.7 psia). In column 110, the HF/254eb azeotrope is used to remove HF from the 245eb-rich feed mixture with very little loss of 245eb. The vapors 120 leaving the top of column 110 are partially condensed in condenser 125 with the resulting condensate 130 returned to the top of 110 as reflux. The non-condensed portion of 120 leaving 125 is removed as distillate 140. Distillate 140 contains essentially all of the HF and 254eb present in feed 100, but only a very small fraction of the 245eb in 100. The operating mass ratio of 130 to 100 is approximately 2.5:1. Essentially all of the 245eb in 100 is removed from the bottom of 110 as the bottoms product via stream 150. Stream 150 is essentially free of both HF and 254eb, demonstrating that the HF/254eb azeotrope has successfully removed HF from the azeotrope formed by HF and 245eb. Compositions of the various streams are indicated in Table 4.

TABLE 4

| Component or variable | 100 column feed mole % | 140 column distillate mole % | 150 bottoms mole % |
|---|---|---|---|
| HF | 0.43 | 5.26 | <0.0001 |
| 245eb | 91.9 | 0.07 | 100 |
| 254eb | 0.41 | 5.04 | <0.0001 |
| H$_2$ | 7.25 | 89.6 | 0 |
| Temp (° C.) | 49.2 | −23.4 | 80.9 |
| Pressure (psia) | 100 | 94.7 | 95.3 |

Example 4

Phase Studies of Mixture of HF and $CF_3CHFCH_3$

A phase study was performed for a composition consisting essentially of $CF_3CHFCH_3$ and HF, wherein the composition was varied and the vapor pressures were measured at both 26.8° C. and 69.4° C. Based upon the data from the phase studies, azeotropic compositions at other temperature and pressures have been calculated.

Table 4 provides a compilation of experimental and calculated azeotropic compositions for HF and $CF_3CHFCH_3$ at specified temperatures and pressures.

TABLE 4

| Temperature ° C. | Pressure psia | Mole % HF | Mole % $CF_3CHFCH_3$ |
|---|---|---|---|
| −40 | 2.7 | 59.3 | 40.7 |
| −30 | 4.6 | 57.0 | 42.9 |
| −20 | 7.6 | 54.9 | 45.1 |
| −10 | 11.9 | 52.9 | 47.1 |
| 0 | 18.1 | 50.9 | 49.1 |
| 10 | 26.6 | 49.0 | 51.0 |
| 20 | 38.0 | 47.2 | 52.8 |
| 26.77 | 47.7 | 46.0 | 54.0 |
| 30 | 52.9 | 45.5 | 54.5 |
| 40 | 72.1 | 43.9 | 56.1 |
| 50 | 96.4 | 42.4 | 57.6 |
| 60 | 127.0 | 41.2 | 58.8 |
| 69.35 | 162.4 | 40.1 | 59.9 |
| 70 | 165.1 | 40.1 | 59.9 |
| 80 | 212.3 | 39.2 | 60.8 |
| 90 | 271.0 | 38.6 | 61.4 |
| 100 | 345.2 | 37.8 | 62.2 |

Example 5

Example 5 demonstrates dew point and bubble point vapor pressures for mixtures of HFC-254eb and HF.

The dew point and bubble point vapor pressures for compositions disclosed herein were calculated from measured and calculated thermodynamic properties. The near-azeotrope range is indicated by the minimum and maximum concentration of HFC-254eb (mole percent, mol %) for which the difference in dew point and bubble point pressures is less than or equal to 3% (based upon bubble point pressure). The results are summarized in Table 5.

TABLE 5

| Temperature, ° C. | Azeotrope composition, mol % HFC-254eb | Near azeotrope compositions, mol % HFC-254eb | |
|---|---|---|---|
| | | Minimum | Maximum |
| −40 | 40.7 | 35.2 | 55.0 |
| 20 | 52.8 | 42.6 | 72.0 |
| 70 | 59.9 | 47.3 | 78.4 |
| 100 | 62.2 | 49.4 | 76.7 |

Example 6

Separation of 254eb from Hydrogen Fluoride by Pressure Swing Distillation

The feed to the pressure-swing distillation is assumed to be a 50/50 molar mixture of HF and 254eb. Referring to Table 4, we can see that a 50/50 mol % feed mixture is on the HF-rich side of the azeotrope at high pressures and very close to the azeotropic composition at 1-2 atm. Consequently, the 50/50 feed is fed to the high pressure column and HF is recovered from the bottom of this column. The distillate from the first column has a composition that approaches the azeotropic composition at the column pressure and is fed to a second distillation column operating slightly above atmospheric pressure. Pure 254eb is recovered from the bottom of the second column and the corresponding distillate stream, which has a composition that approaches the azeotropic composition at the column pressure, which is first pumped to higher pressure and then recycled to the first column.

Referring to FIG. 2, 1000 lb/hr of a 50/50 mol % HF/254eb mixture at elevated pressure (200) is combined with the distillate from the second column (320) to form the overall feed (210) to a first distillation column (220) containing 15 theoretical stages and operating with a top pressure of 264.7 psia (250 psig). Stream 210 is fed to the third theoretical stage from the top of column 220. Because the composition of 210 lies on the HF-rich side of the HF/254eb azeotrope at 250 psig, a first bottoms product can be removed from the bottom of 220 via 230 that contains essentially all of the HF in 200 at a composition that is negligible in 254eb. The distillate 240 from column 220 has a composition that approaches the composition of the HF/254eb azeotrope at 250 psig. This first distillate is cooled by heat exchanger 250 and reduced in pressure across valve 260, forming 270 which is fed to the third theoretical stage from the top of a second distillation column 280. Column 280 contains 15 theoretical stages and operates with a top pressure of 19.7 psia (5 psig). At this pressure, the composition of 270 lies on the 254eb-rich side of the HF/254eb azeotrope so that a second bottoms product can be removed from 280 via 290 that contains essentially all of the 254eb in 200 with a composition that is negligible in HF. A second distillate is removed from 280 via 300 with a composition that approaches the composition of the HF/254eb azeotrope at 5 psig. 300 is increased in pressure across pump 310, forming 320, which is combined with the fresh feed 200 completing the process. Compositions of the various streams are indicated in Table 6.

TABLE 6

| Component or variable | 200 mole % | 210 mole % | 230 mole % | 240 mole % | 290 mole % | 300 mole % |
|---|---|---|---|---|---|---|
| HF | 0.5 | 47.7 | 100 | 41.4 | 1 ppmV | 47.1 |
| 254eb | 0.5 | 52.3 | 1 ppmV | 58.6 | 100 | 52.9 |
| T (° C.) | 25.0 | 8.6 | 124.6 | 89.0 | 7.6 | 2.1 |
| P (psia) | 284.7 | 284.7 | 264.8 | 264.7 | 19.9 | 19.7 |

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. An azeotropic or near-azeotropic composition comprising 1,1,1,2-tetrafluoropropane and hydrogen fluoride.

2. The azeotropic or near-azeotropic composition of claim 1 comprising 1,1,1,2-tetrafluoropropane and an effective amount of hydrogen fluoride.

3. The azeotropic or near-azeotropic composition of claim 1 comprising from about 40.7 mole percent to about 62.2 mole percent 1,1,1,2-tetrafluoropropane, and hydrogen fluoride.

4. The azeotropic or near-azeotropic composition of claim 1 comprising from about 40.7 mole percent to about 62.2 mole percent 1,1,1,2-tetrafluoropropane, and hydrogen fluoride, wherein the vapor pressure is from about 2.6 psia to about 345 psia at a temperature of from about −40° C. to about 100° C.

5. The azeotropic or near-azeotropic composition of claim 1 wherein said composition consists essentially of from about 40.7 mole percent to about 62.2 mole percent 1,1,1,2-tetrafluoropropane, and hydrogen fluoride, wherein the vapor pressure is from about 2.6 psia to about 345 psia at a temperature of from about −40° C. to about 100° C.

6. The azeotropic or near-azeotropic composition of claim 1 comprising from about 35.2 mole percent to about 78.4 mole percent 1,1,1,2-tetrafluoropropane, and hydrogen fluoride, wherein the vapor pressure is from about 2.6 psia to about 345.2 psia at a temperature of from about −40° C. to about 100° C.

7. The azeotropic or near-azeotropic composition of claim 1 wherein said composition consists essentially of from about 35.2 mole percent to about 78.4 mole percent 1,1,1,2-tetrafluoropropane and hydrogen fluoride, wherein the vapor pressure is from about 2.6 psia to about 345.2 psia at a temperature of from about −40° C. to about 100° C.

8. The azeotropic or near-azeotropic composition of claim 1 wherein said composition is characterized by a difference between dew point pressure and bubble point pressure that is less than or equal to 3%, based upon bubble point pressure.

* * * * *